United States Patent
Nho et al.

(10) Patent No.: US 10,829,762 B2
(45) Date of Patent: Nov. 10, 2020

(54) METHOD FOR PREVENTING OR TREATING OBESITY BY USING A COMPOSITION INCLUDING HOGA1-INHIBITING SUBSTANCE AND METHOD OF SCREENING A PREVENTIVE OR THERAPEUTIC AGENT FOR OBESITY BY USING THE COMPOSITION

(71) Applicants: KOREA INSTITUTE OF SCIENCE AND TECHNOLOGY, Seoul (KR); Industry Academic Cooperation Foundation, Hallym University, Chuncheon-si (KR)

(72) Inventors: Chu Won Nho, Seoul (KR); Myung Suk Kim, Seoul (KR); Chang Ho Jhin, Seoul (KR); Yoon Shin Cho, Chuncheon-si (KR); Yeongseon Ahn, Chuncheon-si (KR)

(73) Assignees: KOREA INSTITUTE OF SCIENCE AND TECHNOLOGY, Seoul (KR); INDUSTRY ACADEMIC COOPERATION FOUNDATION, HALLYM UNIVERSITY, Chuncheon-Si (KR)

( * ) Notice: Subject to any disclaimer, the term of this patent is extended or adjusted under 35 U.S.C. 154(b) by 0 days.

(21) Appl. No.: 16/181,835

(22) Filed: Nov. 6, 2018

(65) Prior Publication Data
US 2019/0136243 A1    May 9, 2019

(30) Foreign Application Priority Data
Nov. 6, 2017    (KR) .................. 10-2017-0146944

(51) Int. Cl.
| | | |
|---|---|---|
| *C12N 15/113* | (2010.01) | |
| *A61P 3/04* | (2006.01) | |
| *C07K 16/40* | (2006.01) | |
| *C12Q 1/6876* | (2018.01) | |
| *A61K 31/713* | (2006.01) | |
| *C12Q 1/6883* | (2018.01) | |

(52) U.S. Cl.
CPC ........ *C12N 15/1137* (2013.01); *A61K 31/713* (2013.01); *A61P 3/04* (2018.01); *C07K 16/40* (2013.01); *C12Q 1/6876* (2013.01); *C12Q 1/6883* (2013.01); *C12N 2310/111* (2013.01); *C12N 2310/14* (2013.01); *C12N 2310/16* (2013.01); *C12N 2320/30* (2013.01); *C12Q 2600/136* (2013.01); *C12Q 2600/158* (2013.01)

(58) Field of Classification Search
None
See application file for complete search history.

(56) References Cited

PUBLICATIONS

Kim et al., "Whole exome sequencing suggests Hoga1 associated with obesity," a poster in the KSBMB International Conference dated May 17, 2017, 2 pages.
Li et al., "Hydroxyproline metabolism in a mouse model of Primary Hyperoxaluria Type 3," Biochimica et Biophysica Acta 1852 (2015) 2700-2705.
Monico et al., "Primary Hyperoxaluria Type 10 Gene HOGA1 (Formerly DHDPSL) as a Possible Risk Factor for Idiopathic Calcium Oxalate Urolithiasis," Clinical Journal of the American Society of Nephrology vol. 6, Sep. 2011, 2289-2295.
World Health Organization, "Global Strategy on Diet, Physical Activity and Health," The world health report 2002.

*Primary Examiner* — Tracy Vivlemore
(74) *Attorney, Agent, or Firm* — Birch, Stewart, Kolasch & Birch, LLP

(57) ABSTRACT

Provided are a method for preventing or treating obesity by using a composition including an inhibitor of expression of the Hoga1 gene or an inhibitor of activity of the Hoga1 protein as an active ingredient, and a method of screening a preventive or therapeutic agent for obesity by using the composition.

7 Claims, 9 Drawing Sheets
(4 of 9 Drawing Sheet(s) Filed in Color)
Specification includes a Sequence Listing.

METHOD FOR PREVENTING OR TREATING OBESITY BY USING A COMPOSITION INCLUDING HOGA1-INHIBITING SUBSTANCE AND METHOD OF SCREENING A PREVENTIVE OR THERAPEUTIC AGENT FOR OBESITY BY USING THE COMPOSITION

CROSS-REFERENCE TO RELATED APPLICATION

This application claims the benefit of Korean Patent Application No. 10-2017-0146944, filed on Nov. 6, 2017, in the Korean Intellectual Property Office, the disclosure of which is incorporated herein in its entirety by reference.

REFERENCE TO SEQUENCE LISTING SUBMITTED VIA EFS-WEB

This application includes an electronically submitted sequence listing in .txt format. The .txt file contains a sequence listing entitled "2019-01-07 1183-0127PUS1 ST25.txt" created on Jan. 7, 2019 and is 5,996 bytes in size. The sequence listing contained in this .txt file is part of the specification and is hereby incorporated by reference herein in its entirety.

BACKGROUND

1. Field

One or more embodiments relate to a pharmaceutical or food composition including a substance that inhibits expression of the Hoga1 gene, a method of preventing or treating obesity by using the composition, and a method of screening a preventive or therapeutic agent for obesity by using the composition.

2. Description of the Related Art

Due to recent economic growth and western lifestyle changes, there have been many changes in eating habits. Particularly, in modern times, people have busy lives, and are increasingly overweight and obese because they consume high-calorie diets such as fast food and do little exercise. Obesity is a chronic disease that increases the morbidity and mortality of various diseases due to excessive accumulation of adipose tissue caused by abnormal energy balance control or hypernutrition. Obesity and its related diseases are common and very serious public health problems in the United States, and according to the World Health Organization (WHO), over one billion adults worldwide are overweight, at least three million of which are clinically obese. This phenomenon has increased significantly in the United States and Europe, and in particular, there are 250,000 deaths annually in Europe and more than 25,000 deaths worldwide associated with excessive weight (World Health Organization, Global Strategy on Diet, Physical Activity and Health, 2004).

Excessive weight and obesity increase blood pressure and cholesterol levels, leading to various diseases such as heart disease, diabetes, and arthritis, and increasing the incidence of various adult diseases. In addition, excessive weight and obesity are factors that increase the incidence of various adult diseases such as arteriosclerosis, hypertension, hyperlipidemia, or heart disease, even in children and adolescents as well as adults.

As such, obesity is developing worldwide and causes various diseases but cannot be easily treated. More medical professionals are recognizing that obesity has complex causes and is caused by various factors, and is a complex disease involving regulation of appetite and energy metabolism, not merely a failure of self-control. However, the most common cause of obesity is that energy intake continuously exceeds energy consumed. Therefore, there is a need for effective and safe medicines that can be used together with diet and exercise in the long term to prevent or treat obesity.

As a preventive or therapeutic agent for obesity, the inventors of the present specification have made intensive efforts to find a safe substance that does not affect the body, and have discovered the relationship between the Hoga1 gene and obesity for the first time. Furthermore, the inventors have suggested a novel obesity treatment target and provided a composition containing an inhibitor of expression of the Hoga1 gene or an inhibitor of activity of the Hoga1 protein as an active ingredient, a method of screening the same, and a method of treating obesity by using the same.

SUMMARY

An aspect provides a composition including an inhibitor of expression of the Hoga1 gene or an inhibitor of activity of the Hoga1 protein as an active ingredient.

An aspect provides a method of preventing or treating obesity, the method including administering a composition including the inhibitor of expression of the Hoga1 gene or the inhibitor of activity of the Hoga1 protein.

An aspect provides a method of screening a preventive or therapeutic agent for obesity, the method including:

(a) bringing cells or Hoga1 protein into contact with a test material, thereby obtaining a contacted mixture;

(b) measuring the expression level of mRNA of the Hoga1 gene in the contacted mixture or the expression level or activity level of the Hoga1 protein in the contacted mixture; and (c) comparing the expression level or activity level measured in operation (b) with the expression level and activity level of a control.

BRIEF DESCRIPTION OF THE DRAWINGS

The patent or application file contains at least one color drawing. Copies of this patent or patent application publication with color drawing will be provided by the USPTO upon request and payment of the necessary fee.

These and/or other aspects will become apparent and more readily appreciated from the following description of the embodiments, taken in conjunction with the accompanying drawings in which.

DETAILED DESCRIPTION

Figure 1:
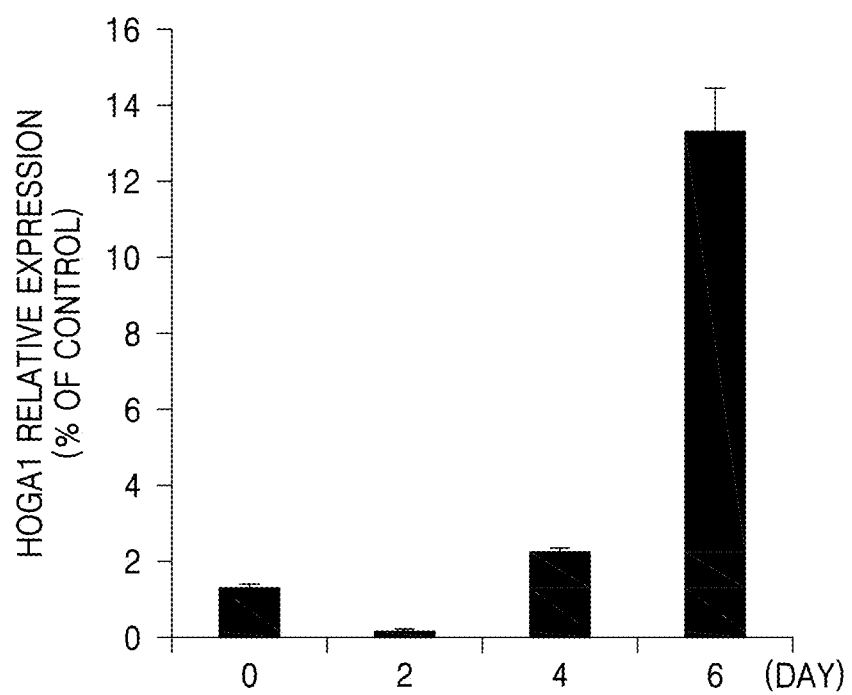
FIG. 1 is a graph obtained by quantifying the mRNA expression of Hoga1 by RT-PCR.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

An aspect provides a composition including an inhibitor of expression of the Hoga1 gene or an inhibitor of activity of the Hoga1 protein as an active ingredient.

An aspect provides a method of preventing or treating obesity, the method including administering a composition including the inhibitor of expression of the Hoga1 gene or the inhibitor of activity of the Hoga1 protein.

The term "Hoga1 gene" [NCBI ID: 67432 (Mus musculus), ID: 112817 (Homo sapiens)] used herein refers to a gene encoding the Hoga1 protein. The Hoga1 gene is mainly expressed in the liver and kidney, and a Hoga1 protein is a protein having the size of 35 kDa and an enzyme involved in the final step of biosynthesis of hydroxyproline that is a precursor of collagen (Biochim Biophys Acta. 2015, 1852 (12), 2700-2705). Due to this enzymatic action, glyoxylate and pyruvate may be generated. Mutations of Hoga1 gene may cause type III primary hyperoxaluria (Clin J Am Soc Nephrol. 2011, 6 (9), 2289-2295), and a gene that interacts with Hoga1 gene may include GOT1, GOT2, HAO1, HAO2, and GRHPR.

The term "inhibitor of the expression of Hoga1 gene" refers to a material that reduces the expression or activity of the Hoga1 gene in a cell, and may be a nucleic acid, a polypeptide, a protein, or a combination thereof that specifically binds to the Hoga1 gene. In detail, the inhibitor of the expression of Hoga1 gene refers to a material that reduces the expression level or activity of Hoga1 gene either by reducing the expression of the Hoga1 gene at the transcription level by an action direct on the Hoga1 gene or an action indirect on the upstream regulator of the Hoga1 gene or by increasing the decomposition of the expressed Hoga1 gene or interfering the activity thereof. Such a material includes, but are not limited to, biological molecules such as nucleic acids or polypeptides, compounds, or extracts isolated from bacteria, plants or animals, which inhibit the gene and is applicable to cells by using a standard technique known in the art. Examples of the inhibitor of the expression of Hoga1 gene are an antisense oligonucleotide, short interfering RNA (siRNA), short hairpin RNA (shRNA), an aptamer, ribozyme, and a low molecular compound, each complementarily binding to the mRNA of the Hoga1 gene. For example, the expression inhibitor may be an antisense oligonucleotide, an siRNA, an alphamer, or a combination thereof, each of which binds to the Hoga1 gene, The term "antisense oligonucleotide" used herein refers to a naturally occurring nucleotide consisting of bases, sugars and intersugar linkages, or an oligomer or polymer of nucleoside monomers. This term also includes modified or substituted oligomers including non-naturally occurring monomers or portions thereof that function similarly. The incorporation of substituted oligomers is based on factors including increased cell uptake or increased nuclease resistance and may be selected as known in the art. The entire oligonucleotide or portion thereof may contain a substituted oligomer. In addition, the antisense oligonucleotides according to the present disclosure may include oligomer mimetics modified by methods known in the art to increase their affinity for their targets and provide resistance to mismatch of the target sequence. Examples of the modified oligomer mimetics are a peptide nucleic acid (PNA) and a locked nucleic acid (LNA). In one embodiment, the antisense oligonucleotide may be natural oligonucleotide, phosphorothioate-type oligodeoxyribonucleotide, phosphorodithioate type oligodeoxyribonucleotide, methylphosphonate type oligodeoxyribonucleotide, phosphoramidate type oligodeoxyribonucleotide, H-phosphonate type oligodeoxyribonucleotide, triester type oligodeoxyribonucleotide, alpha-anomer type oligodeoxyribonucleotide, and a modified oligonucleotide including peptide nucleic acids, other synthetic nucleic acids and nucleic acid-modified compounds, but is not limited thereto. An antisense oligonucleotide molecule that binds complementarily to the Hoga1 nucleotide sequence may be isolated or prepared by using standard molecular biology techniques, such as chemical synthesis methods or recombinant methods. In one embodiment, commercially available antisense oligonucleotide molecules may be used therefor.

The term "short interfering RNA (siRNA)" refers to a double-stranded RNA that induces RNA interference (RNAi) by acting specifically on Hoga1 gene to cleave Hoga1 RNA. siRNA may be provided as an efficient gene knockdown method or as a gene therapy method because siRNA inhibits the expression of the target gene. siRNA was first discovered in plants, insects, fruit flies and parasites, but recently siRNA has been developed and used in the research into mammalian cells. The siRNA for the Hoga1 gene may include a nucleotide sequence that consists of a sense RNA strand including a sequence homologous to some or all of the Hoga1 gene nucleic acid sequence and an antisense RNA strand including a complementary sequence thereto and thus is hybridizable to the Hoga1 RNA in the cell. The siRNA is not limited to a case in which, regarding a double-stranded RNA where RNA portions are paired with each other, the RNA portions are completely paired each other, and may include the case of a mismatch, that is, non-complementary corresponding bases and the case of bulge, that is, absence of a base corresponding to one chain. The full length of the siRNA may be from 10 to 100 bases, for example, from 15 to 80 bases, from 20 to 70 bases, or from 20 to 30 bases. The siRNA molecule may have a short nucleotide sequence inserted between the self-complementary sense and antisense strand, for example, about 5-15 nt nucleotide sequence. In this case, a siRNA molecule formed by the expression of the nucleotide sequence may form a hairpin structure due to intramolecular hybridization, and as a whole, form a stem-and-loop structure. This stem-and-loop structure is processed in vitro or in vivo to produce an active siRNA molecule capable of mediating RNAi.

The term "short hairpin RNA" refers to an RNA molecule having an RNA sequence that produces a tight hairpin turn that may be used to silence gene expression through RNA interference. The shRNA hairpin structure is cleaved into siRNA by cellular mechanism, which in turn may be bound to an RNA-induced silencing complex (RISC). This complex may be cleaved by binding to mRNA matched to the siRNA bound thereto. The sequence of the siRNA may correspond to a full-length target gene or subsequence thereof. The siRNA is "targeted" to the gene. In detail, the nucleotide sequence of the duplex portion of the siRNA may be substantially complementary to the nucleotide sequence of the targeted gene. The siRNA sequence duplex needs to be long enough to bring the siRNA together through complementary base-pairing interactions to target the RNA, and may have various lengths. The length of the siRNA may be at least 10 nucleotides, and may be a length sufficient to stably interact with the target RNA; 10-30 nucleotides; or nucleotides in any integer between 10 and 30, such as 10, 11, 12, 13, 14, 15, 16, 17, 18, 19, 20, 21, 22, 23, 24, 25, 26, 27, 28, 29, and 30. The "sufficient length" refers to 10 or more nucleotides that is long enough to provide the target function under the expected conditions. The shRNA may be cloned into a vector using recombinant DNA technology.

The term "aptamer" refers to a nucleic acid ligand molecule that binds to a Hoga1 gene due to an ability to adopt a specific three-dimensional form and thus has an antagonistic effect thereto. For example, the aptamer may be a nucleic acid having the length of 15 to 50 bases which constitute a defined secondary and tertiary structure, for example, a structure that folds into a stem-loop structure. The aptamer may bind to the target molecule at a kD of less than 10-6, 10-8, 10-10, or 10-12. The aptamer may bind to a target molecule with a very high specificity. In one embodiment, an aptamer may consist of a plurality of ribonucleotide units, deoxyribonucleotide units, or a mixture of two types of nucleotide residues. The aptamer may further include one or more modified backbone units each consisting of base, sugar or phosphate.

The term "ribozyme" refers to an RNA molecule having a catalytic activity. Ribozyme with various activities is known. The ribozyme of the Hoga1 gene includes known or artificially generated ribozyme, and optionally ribozyme with target-specific RNA cleaving activity may be prepared by standard techniques known in the art.

The term "low molecular compound" refers to a natural or non-naturally occurring chemical material other than a biopolymer present in a living body, and may be a target tissue-specific compound or non-natural compound, but is not limited thereto.

The term "inhibitor of the activity of Hoga1 protein" refers to a material that reduces the activity or action of the Hoga1 protein encoded by the Hoga1 gene, and may be peptides, peptide mimetics, substrate analogs, compounds, antibodies, or combinations thereof, each specifically binding to the Hoga1 protein. In one embodiment, the inhibitor may be polyclonal antibodies, monoclonal antibodies, or recombinant antibodies, each of which binds to the Hoga1 protein. The peptide mimetics refer to a compound that is a therapeutic agent and mimics the structure and characteristics of a particular polypeptide.

The sequence of the Hoga1 gene may be easily obtained by one of ordinary skill in the art from a known database such as GenBank. Thus, an antisense oligonucleotide, an siRNA, an aptamer, and an antibody which inhibit the expression of the gene may be prepared by using the obtained sequence according to a known standard technique.

The term "antibody" refers to a specific protein molecule directed against an antigenic site capable of binding to Hoga1 protein and inhibiting the activity of Hoga1. The antibody refers to an antibody that specifically binds to Hoga1 protein, and includes polyclonal antibodies, monoclonal antibodies, and recombinant antibodies. Since the Hoga1 protein has been identified, antibodies against the Hoga1 protein may be readily prepared by using techniques well known in the art. The polyclonal antibody may be produced by a well-known method in the art, in which the Hoga1 protein antigen described above is injected into an animal and blood is drawn from the animal to obtain serum containing the antibody. The polyclonal antibody may be prepared from any animal host, such as goats, rabbits, sheep, monkeys, horses, pigs, cows, dogs, and the like. The monoclonal antibody may be prepared using a hybridoma method, or a phage antibody library technique, each being well known in the art. The antibody produced by the above method may be separated and purified by gel electrophoresis, dialysis, salt precipitation, ion exchange chromatography, affinity chromatography, and the like. In addition, the antibody according to the present disclosure may include a functional fragment of an antibody molecule as well as a complete form having two full-length light chains and two full-length heavy chains. The functional fragment of an antibody molecule refers to a fragment having at least an antigen binding function, and may include, for example, Fab, F(ab'), F(ab')2, and Fv.

People who have excessive adipose tissues in the body, not high body weight, are defined to be obese, because even people who have a lot of muscles may also have high body weight. The term "obesity" refers to an excess of body fat, and clinically refers to a body mass index of 25 in Korea and 30 or more according to the World Health Organization (WHO). In general, obesity means that the body weight is higher than a normal level. However, people who have relatively low body weight may also be diagnosed as being obese when they have a high proportion of body fat among the constituents of the body in the body. Obesity occurs in adults and children. Obesity may induce an increased body weight, and overeating, crapulence, and bulimia, and obesity-associated disorders, such as hypertension, diabetes, increased plasma insulin levels, insulin resistance, hyperlipidemia, metabolic syndrome, insulin resistance syndrome, obesity related gastroesophageal reflux, arteriosclerosis, hypercholesterinemia, hyperuricacidemia, lower back pain, cardiac hypertrophy and left ventricular hypertrophy, lipodystrophy, nonalcoholic fatty liver disease, cardiovascular disease, or polycystic ovarian syndrome. Therefore, when the composition according to the present disclosure is used, not only obesity but also the obesity-related diseases may be prevented or treated at the same time. A subject of which obesity-related diseases are to be treated includes a subject who has a desire to lose weight.

The term "treatment" refers to any action in which a disease, disorder, or ancillary symptoms thereof is alleviated or beneficially altered. Such treatment may include alleviation of symptoms, reduction in disease severity, maintenance of non-aggressive disease, delayed disease progression, improvement or alleviation of disease state, (partial or complete) relief. The treatment may also refer to an improved condition compared to the expected disease state when not treated, and may include prophylactic measures in addition to therapeutic measures. The case in which when treatment is needed refers to the case where the disease is already present and the case where the disease should be prevented. The relief of disease may refer to, compared to untreated conditions, improvement in the clinical presentation of unwanted disease or a delay or prolongation of disease progression. For example, the treatment refers to any action that alleviates or beneficially alters symptoms of an obesity or obesity-related disorder upon administration of a composition according to the present disclosure.

The term "prevention" refers to partially or completely delaying or preventing the onset or recurrence of a disease, disorder, or ancillary symptoms thereof, or preventing the acquisition or reacquisition of the disease or disorder, or reducing the risk of acquiring the disease or disorder. For example, the prevention refers to any act that inhibits or delays the occurrence of obesity, or the obesity, disorder, or symptom related disorder by administration of a composition according to the present disclosure.

According to one embodiment, in the case of a mouse of which Hoga1 gene is knockdown by using siRNA, it was confirmed that an increase in body weight due to obesity induced by a high-fat diet is inhibited, the size of adipose tissue is decreased, and the sizes of adipocytes is decreased. Also, a composition including a material that inhibits the expression of the gene has been found capable of preventing or treating obesity.

According to one embodiment, the composition according to the present disclosure may include at least one of an inhibitor of the expression of Hoga1 gene and an inhibitor of the activity of Hoga1 protein as an active ingredient, and further includes a pharmaceutically acceptable carrier, and may be formulated with a carrier.

The term "pharmaceutically acceptable carrier" refers to a carrier or diluent that does not irritate the organism and does not interfere with the biological activity and properties of the administered compound. Examples of the pharmaceutical carrier that is acceptable for the composition to be formulated into a liquid solution include any carrier that is suitable for living body, such as saline, sterile water, Ringer's solution, buffered saline, albumin injection solution, dextrose solution, maltodextrin solution, glycerol, ethanol, or a mixture of at least one component thereof. If needed, such a pharmaceutically acceptable carrier may further include antioxidants, buffers, bacteriostats. In addition, diluents, dispersants, surfactants, binders, and lubricants may be additionally added thereto to prepare injectable formulations such as aqueous solutions, suspensions, emulsions, or pills, capsules, granules or tablets.

According to one embodiment, the composition according to the present disclosure may be a pharmaceutical or food composition including at least one of an inhibitor of the expression of Hoga1 gene and an inhibitor of the activity of Hoga1 protein and a pharmaceutically acceptable carrier. The composition may be applied to any pharmaceutical or food formulation containing the composition as an active ingredient, and may be formulated into oral or parenteral formulations and may be formulated into unit dosage forms for ease of administration and uniformity of dosage.

The pharmaceutical formulations may have a shape that is suitable for an oral administration, a rectal administration, a nasal administration, a topical administration (including cheeks and under tongue), a subcutaneous administration, a vaginal administration, or a parenteral administration (including intramuscular, subcutaneous and intravenous administration), and for an inhalation administration or insufflation administration.

The formulation for oral administration including the pharmaceutical composition according to the present disclosure as an active ingredient may be, for example, tablets, troches, lozenges, water-soluble or oily suspensions, prepared powders or granules, emulsions, hard or soft capsules, syrups or elixirs. The formulation into tablets and capsules may include a binder such as lactose, saccharose, sorbitol, mannitol, starch, amylopectin, cellulose or gelatin; an excipient such as dicalcium phosphate; a disintegrating agent such as corn starch or sweet potato starch; and lube oil such as magnesium stearate, calcium stearate, sodium stearyl fumarate, or polyethylene glycol wax. In the case of the capsule formulation, in addition to the materials described above, the formulation may further include a liquid carrier, such as fatty oil.

Examples of the parenteral administration formulations containing the pharmaceutical composition according to the present disclosure as an active ingredient include an injectable formulation such as subcutaneous injections, intravenous injections, or intramuscular injections; a suppository injection forms; or a spray formulation, for example, an aerosol preparation, that allows inhalation through respirators. For formulation into injectable formulations, the composition according to the present disclosure may be formulated as a solution or suspension in water together with a stabilizer or buffer, and may be formulated for unit administration of an ampoule or vial. For insufflation with suppositories, compositions may be formulated for rectal administration, such as suppositories or enema, including suppository bases of the related art such as cocoa butter or other glycerides. When formulated for spraying, such as an aerosol formulation, a propellant or the like may be formulated with the additive such that the water-dispersed concentrate or wet powder is dispersed.

One embodiment relates to a method of preventing or treating obesity, the method including administering a pharmaceutical composition for the prevention or treatment of obesity, the pharmaceutical composition including an inhibitor of the expression of the Hoga1 gene or an inhibitor of the activity of the Hoga1 protein.

The term "administration" used herein refers to introducing the pharmaceutical composition according to the present disclosure to the patient in any suitable manner. When the composition according to the present disclosure is introduced into a subject, obesity may be prevented or treated by weight loss, a reduction in the size of adipose tissue, and a reduction in the size of adipocytes. The administration route for the composition may be oral or parenteral as long as the composition reaches the target tissues. In one embodiment, the composition may be administered in a manner of the related art via the oral, rectal, topical, intravenous, intraperitoneal, intramuscular, intraarterial, transdermal, intranasal, inhalation, intraocular, or intradermal routes.

The method of preventing or treating obesity may include administering the pharmaceutical composition according to the present disclosure in a therapeutically effective amount.

The therapeutically effective amount may refer to an amount that promotes weight loss or reduction in the size of adipocytes It is apparent to those skilled in the art that the appropriate total daily dose may be determined by the practitioner within the scope of correct medical judgment. The specific therapeutically effective amount for a particular patient depends upon a variety of factors, including the type and extent of the response to be achieved, whether or not other agents are used, specific composition to be administered, the age, weight, general health status, sex and diet, administration time, administration route, and release rate of the composition, duration of treatment, and various factors and similar factors well known in the medical art. Therefore, it is desirable to determine the effective amount of the pharmaceutical composition for the prevention or treatment of obesity suitable for the purpose of the present disclosure, by taking into consideration the above-mentioned factors. In addition, in combination with the composition according to the present disclosure, a known therapeutic agent for obesity-related diseases may be administered to increase the therapeutic effect of obesity-related diseases, including obesity inhibition.

In addition, the treatment method according to the present disclosure is applicable to any animal capable of preventing or inhibiting obesity, and the animal may include not only humans and primates but also livestock such as cows, pigs, sheep, horses, dogs, and cats.

Another embodiment provides a food composition for preventing or ameliorating obesity, the composition including, as an active ingredient, an inhibitor of the expression of Hoga1 gene or an inhibitor of the activity of Hoga1 protein. The inhibitor of the expression of the Hoga1 gene or the inhibitor of the activity of the Hoga1 protein is the same as described above. According to one embodiment, the food composition according to the present disclosure may include at least one of an inhibitor of the expression of Hoga1 gene and an inhibitor of the activity of Hoga1 protein, and a carrier that is acceptable for food, and may be formulated with the carrier. The food composition may be in the form of pills, powders, granules, infusions, tablets, capsules or liquids. Examples of the foods to which the composition according to the present disclosure is added include various foods, beverages, gums, tea, vitamin complex, health supplement foods, and the like. The food composition according to the present disclosure may be used as a food additive because of a small side effect such as a decrease in appetite or activity. As an essential ingredient for the food composition for the ameliorating obesity, there are no particular restrictions on other ingredients than the composition including a material that inhibits the expression of the Hoga1 gene. Like food of the related art, the food composition according to the present disclosure may include various herbal medicine extracts, food additives, or natural carbohydrates. Since food additives may also be added as mentioned above, food additives may include any food additive of the related art, such as nutrients, vitamins, minerals (electrolytes), flavors, colorants, fillers, stabilizers, and the like. Examples of such natural carbohydrates are monosaccharides such as glucose, fructose, etc.; disaccharides such as maltose, sucrose, etc.; and polysaccharides, for example, sugars of the related art such as dextrin, cyclodextrin, etc, and sugar alcohols such as xylitol, sorbitol, and erythritol. Other than those described above, natural flavors (tau martin, stevia extracts (e.g., rebaudioside A, glycyrrhizin, etc.) and synthetic flavors (saccharin, aspartame, etc.) may be advantageously used as flavors. The food composition may further include natural fruit juice and fruit pulp for the production of fruit juice drinks and vegetable drinks. These components may be used independently or in combination. The food composition for the amelioration of obesity may be provided in the form of a health functional food.

The term "health functional food" refers to a food prepared, for the maintenance of health, by preparing, processing a specific ingredient as a raw material or by extracting, concentrating, refining, or mixing a specific ingredient contained in the raw material of the food. The health functional food is designed or processed to sufficiently exert a biological control function such as bio-defense, regulation of biological rhythm, the prevention and recovery of disease due to such components. The composition for health food may perform functions related to the prevention of obesity and the recovery of obesity related diseases.

Another aspect provides a method of screening a preventive or therapeutic agent for obesity, the method including: (a) bringing cells or Hoga1 protein into contact with a test material, thereby obtaining a contacted mixture;
(b) measuring the expression level of mRNA of Hoga1 gene in the contacted mixture or the expression level or activity level of Hoga1 protein in the contacted mixture; and
(c) comparing the expression level or activity level measured in operation (b) with the expression level and activity level of a control.

The cells refer to a cell expressing the Hoga1 gene. The cells may be contained in a subject The term "subject" refers to a subject or sample to be treated with a test material for screening for a preventive or therapeutic agent for obesity. The subject may be, but is not limited to, a mammal selected from horses, dogs, cows, pigs, monkeys, chimpanzees, rabbits, chickens, mice, rats, guinea pigs, and humans. The sample may be, but is not limited to, whole blood, serum, blood, plasma, saliva, urine, sputum, lymph, and cells, all of which are separated from the subject. For example, the subject may be a subject that is suspected to have obesity.

The method of measuring the mRNA expression level of the gene refers to a method of measuring the level of the mRNA transcribed from the target gene to confirm the expression of the target gene contained in the sample, and examples thereof are RT-PCR, competitive RT-PCR, real-time RT-PCR, RNase protection assay (RPA), northern blotting, DNA chip analysis, and are not limited thereto.

The method of measuring the expression level or activity level of the protein refers to a method of measuring the expression level or activity level of the target protein contained in the sample, and examples thereof are western blotting, enzyme linked immunosorbent assay (ELISA), radioimmunoassay (RIA), radioimmunodiffusion, ouchterlony immunoassay, rocket immunoelectrophoresis, tissue immunostaining, immunoprecipitation assays, complement fixation assays, FACS, and protein chip assay, and are not limited thereto.

The term "contact" may be substituted for treatment or administration, and the contacting process may include administering the test material to the subject. For example, the administration may refer to treating a subject containing a cell that expresses Hoga1 gene or a subject that expresses Hoga1 protein with a test material. The administration may be carried out via various routes through which the test material may be delivered to the subject. In one embodiment, the test material may be administered, for example, orally or rectally, or by intravenous, muscular, subcutaneous, intrauterine, or intracerebral injection.

The term "measurement" includes a series of deductive and inductive processes that utilize specific data to derive an unknown value. The measurement may be substituted for calculation, prediction, identification, or determination.

According to one embodiment, the cells in (a) are contained in a subject, and the process of contacting may include administering a test material to a subject.

The contacted mixture is formed by the contact with the test material and refers to a mixture capable of detecting one or more expression levels or activity levels associated with the Hoga1 gene or Hoga1 protein.

The term "test material" refers to a drug that tests the change in the activity of the Hoga1 gene or the Hoga1 protein, and may be used in place of "candidate material."

The test material is an object to measure the ability to prevent or treat obesity by directly or indirectly changing the expression level of Hoga1, and may be replaceable for a test composition or a test compound, and examples thereof may include a molecule, such as a protein, an oligopeptide, a small organic molecule, a polysaccharide, a polynucleotide, and a variety of compounds. The test material may include a natural material and a synthetic material and may include a candidate material that may be used as an obesity therapeutic agent. For example, the test material may be an antisense oligonucleotide, a short interfering RNA (siRNA), a short hairpin RNA (shRNA), an aptamer, a ribozyme, a low molecular compound, an antibody, a peptide, peptide mimetics, substrate analogs, or proteins, but is not limited thereto.

The term "control" refers to a subject that has not been in contact, administered or treated with a test material.

The screening method according to an embodiment further includes selecting the test material as a preventive or therapeutic agent for obesity when the expression level or the activity level measured in the process (b) is lower than the expression level or the activity level of the control.

The term "therapeutic agent for obesity (remedy for obesity)" refers to a material that prevents or treats obesity by weight loss, a decrease in the size of adipose tissue, and a decrease in the size of adipocyte.

The screening method according to an embodiment of the present disclosure may be performed in such a way that a subject or an obesity suspect subject is treated with a test material or a candidate material for the treatment of obesity, and then the expression level of Hoga1 gene mRNA or the expression or activity level of Hoga1 protein of the subject or obesity suspect subject is compared with those of a control that has not been treated with the test material or candidate material, and when the expression level of Hoga1 gene mRNA or the expression or activity level of Hoga1 protein of the subject or obesity suspect subject is lower than those of the control, the corresponding test material and candidate material is determined as a preventive or therapeutic agent for obesity. The analysis to measure the expression level of mRNA includes, but is not limited to, reverse transcriptase polymerase, competitive reverse transcriptase polymerase, real-time reverse transcriptase polymerase, RNase protection assay, northern blotting, or use of DNA chip. The analysis to measure the expression level of the Hoga1 protein includes, but is not limited to, western blotting, ELISA, radioimmunoassay, radial immunodiffusion, rocket immunoelectrophoresis, tissue immuno staining, immunoprecipitation assay, complement fixation assay, FACS, or use of a protein chip.

The composition according to the present disclosure may be used as a preventive or therapeutic agent for obesity which is capable of preventing the weight gain and reducing the size of adipocytes without no change in energy consumption and activity amount. A treatment method using the composition may effectively treat obesity.

Hereinafter, the present disclosure will be described in more detail with reference to examples. However, these examples are provided herein for illustrative purpose only, and do not limit the scope of the present disclosure.

Example 1. Confirmation of Differentiation of Lipid Precursor Cells and Expression of Hoga1

3T3-L1 lipid precursor cells were maintained in Dulbecco modified eagle medium (DMEM) containing 10% bovine serum (Invitrogen, Carlsbad, Calif., USA). DMEM supplemented with 5 mg/ml insulin, 0.25 mmol/l dexamethasone and 0.5 nmol/l 3-isobutyl-alpha-methylxanthine (IBMX) and containing 10% bovine serum was added thereto to induce differentiation into adipocytes. After 2 days, while the medium was changed every other day with DMEM containing 10% bovine serum and 1 mg/ml insulin, cells were maintained for 6 days after the start of differentiation.

RNA was obtained at the differentiation time points of 2 days, 4 days, and 6 days to confirm expression of Hoga1. Specifically, after 24 hours, the total RNA was harvested from the cells using TRIzol reagent (Invitrogen, Carlsbad, Calif., USA) and reverse transcribed, and then RT-PCR was performed thereon as follows. First, for cDNA synthesis, the RNA was reverse transcribed by using reverse transcriptase. RT-PCR was performed by using the specific primers shown in Table 1. The relative mRNA expression level of the Hoga1 gene was normalized to the value of β-actin.

TABLE 1

| Mice | β-actin | Hoga1 |
| --- | --- | --- |
| Forward primer (F) | SEQ ID NO: 1 | SEQ ID NO: 3 |
| Reverse primer (R) | SEQ ID NO: 2 | SEQ ID NO: 4 |

FIG. 1 is a graph obtained by quantifying the mRNA expression of Hoga1 by RT-PCR. As shown in FIG. 1, mRNA expression of Hoga1 was increased upon differentiation of 3T3-L1 lipid precursor cells.

Example 2. Confirmation of Inhibition of Hoga1 Expression and Inhibition of Adipocyte Differentiation by siRNA Treatment 3T3-L1 lipid precursor cells were maintained in DMEM containing 10% bovine serum (Invitrogen, Carlsbad, Calif., USA). Differentiation into adipocytes was induced by addition of DMEM including 5 mg/ml insulin, 0.25 mmol/l dexamethasone and 0.5 nmol/l 3-isobutyl-α-methylxanthine, IBMX, and containing 10% bovine serum. After 2 days, while the medium was changed every other day with DMEM containing 10% bovine serum and 1 mg/ml insulin, cells were maintained by 6 days. At the same time, Hoga1 siRNA (Genolution, Seoul, Korea) was added to the medium at a concentration of 10 μM once every three days. The degree of differentiation of lipid precursor cells was measured by Oil Red O staining (Sigma-Aldrich, Louis, Mo., USA). After 6 days, the expression of adipocyte differentiation marker gene was confirmed by RT-PCR assay. Specifically, after 24 hours, the total RNA was harvested from the cells using TRIzol reagent (Invitrogen, Carlsbad, Calif., USA) and reverse transcribed, and then RT-PCR was performed thereon. First, for cDNA synthesis, the RNA was reverse transcribed by using reverse transcriptase. The sequence of the Hoga1 siRNA is as shown in Table 2, and RT-PCR was performed by using the specific primers shown in Table 3. The relative mRNA expression level of each gene was normalized to the value of β-actin.

TABLE 2

| Mouse | Control siRNA | Mouse Hoga1 siRNA |
|---|---|---|
| Sense | SEQ ID NO: 5 | SEQ ID NO: 7 |
| Antisense | SEQ ID NO: 6 | SEQ ID NO: 8 |

TABLE 8

| Mouse | β-actin | PPARγ | aP2 | CD36 | C/EBPα |
|---|---|---|---|---|---|
| Forward Primer (F) | SEQ ID NO: 1 | SEQ ID NO: 9 | SEQ ID NO: 11 | SEQ ID NO: 13 | SEQ ID NO: 15 |
| Reverse Primer (R) | SEQ ID NO: 2 | SEQ ID NO: 10 | SEQ ID NO: 12 | SEQ ID NO: 14 | SEQ ID NO: 16 |

Figure 2A:
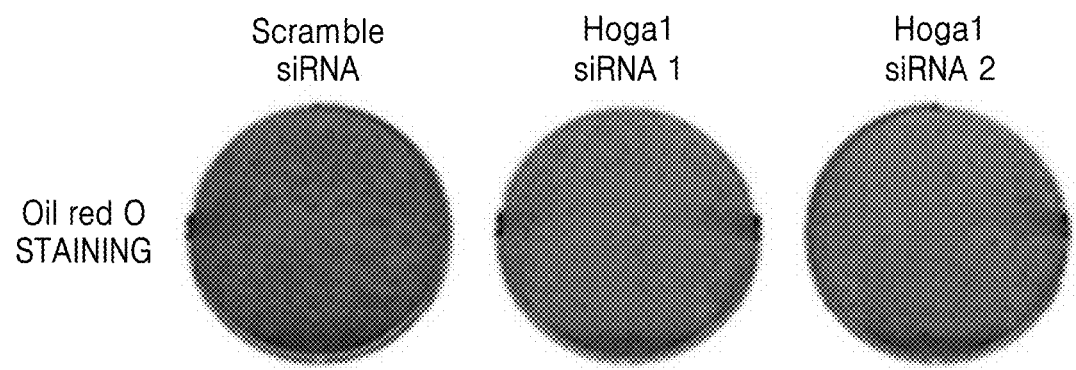
FIG. 2A shows images of oil red O staining of lipid precursor cells of which differentiation is induced for one week by the addition of Hoga1 siRNA.
Figure 2B:
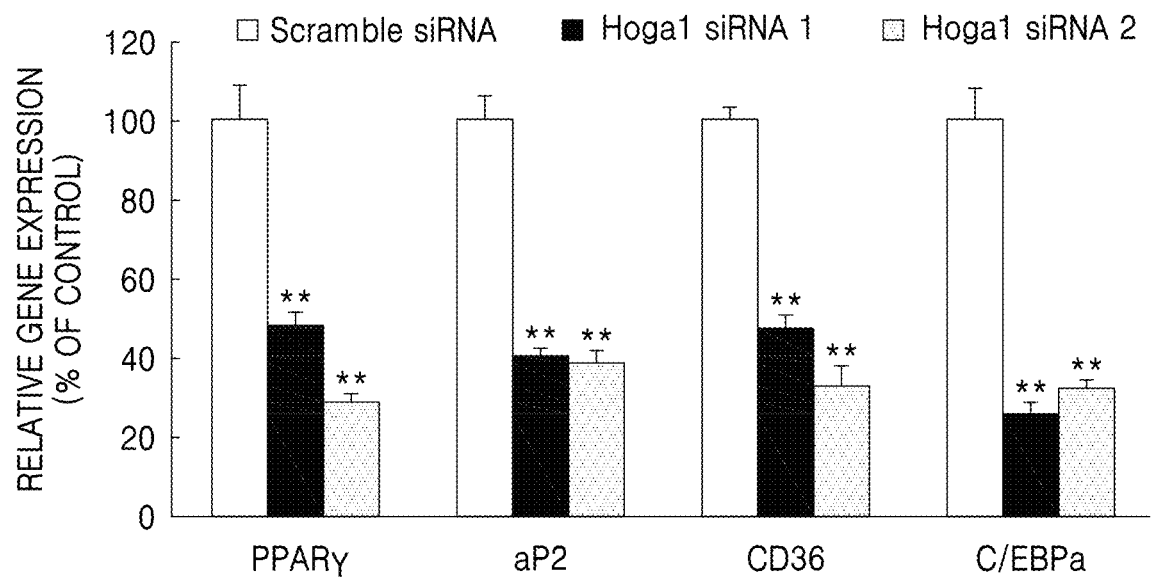
FIG. 2B is a graph showing the expression levels of PPARγ, aP2, CD36, and C/EBPα, which are adipocyte differentiation markers.

FIGS. 2A and 2B show the effect of Hoga1 siRNA on the differentiation of adipocyte. FIG. 2A shows an image of cells stained with oil red O after their differentiation was induced for 1 week. FIG. 2B is a graph showing the expression of PPARγ, aP2, CD36, and C/EBPα, which are adipocyte differentiation markers, confirmed by RT-PCR after obtaining RNA of cells.

As shown in FIG. 2A and FIG. 2B, when treated with Hoga1 siRNA, differentiated lipid precursor cells showed inhibition of lipid accumulation and inhibition of the expression of adipocyte differentiation markers.

Example 3. Weight Change of Hoga1 siRNA Treatment and High-Fat Diet Obesity-Induced Mice C57BL/6 mice (male, 4 weeks old) were obtained from the Central Animal Experiment and obesity thereof was induced to obtain diet induced obese mice (DIO mice) by providing a high-fat diet (60% fat calorie, Diet Research # D12492) for 8 weeks obese mice), and normal controls were provided with an ordinary diet (standard chow, 13.5% fat calorie, Lab diet #5001).

The mice were divided into five test groups (n=8 per group) according to body weight, and a normal diet was fed to normal control mice (test group 1) for 8 weeks, and a high-fat diet was fed to obesity-induced mice (test groups 2 to 5). The cycle of dark and light was maintained at the intervals of 12 hours of dark and 12 hours of light, and the mice was allowed to drink water freely. The dietary, dosage, and administration methods applied to the test groups are shown in Table 4 below. The test material was prepared in the form of a liquid preparation which was a suspension by using 3% CMC, and administered for 8 weeks. In addition, to compensate for the placebo effect of 3% CMC and weight loss effects caused by the administration stress, a vehicle control was daily administered with 3% CMC.

TABLE 4

| Test group | Food | Test material | Dosage and administration method |
|---|---|---|---|
| 1 | Normal diet | Vehicle | — |
| 2 | high-fat diet | Vehicle | — |
| 3 | | Hoga1 siRNA | 20 mg/kg, twice a week |

After 8 weeks of peritoneal administration of Hoga1 siRNA, the serum, liver and adipose tissues were removed from all the administration groups and then weighed, and obesity-related index in serum and tissues were confirmed. Mice that were fed with the normal diet and different high-fat diets for 8 weeks were weighed to measure their body weights once a week, and for each group, the substantially measured body weight and a difference between the body weight at the beginning and the substantially measured body weight were recorded. Subsequently, mice that underwent normal diet and high-fat diet for 12 weeks were autopsied and the liver tissue and white adipose tissue thereof were observed and weighed.

Figure 3:
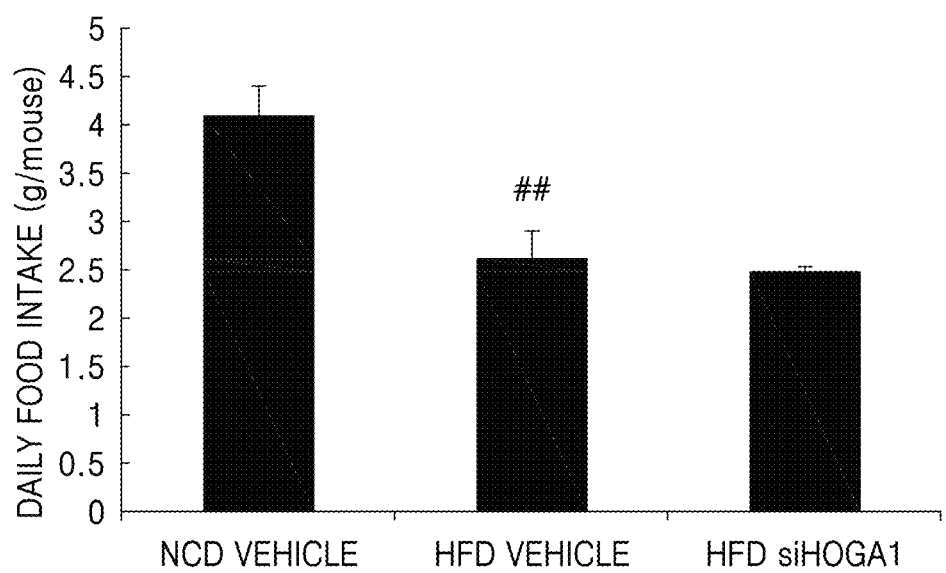
FIG. 3 is a graph showing the food intake of wild-type (NCD vehicle), high-fat diet (HFD vehicle), and a combination of high-fat diet and Hoga1 siRNA (HFD siHOGA1)-treated mice (hereinafter referred to as "each test group") provided.
Figure 4:
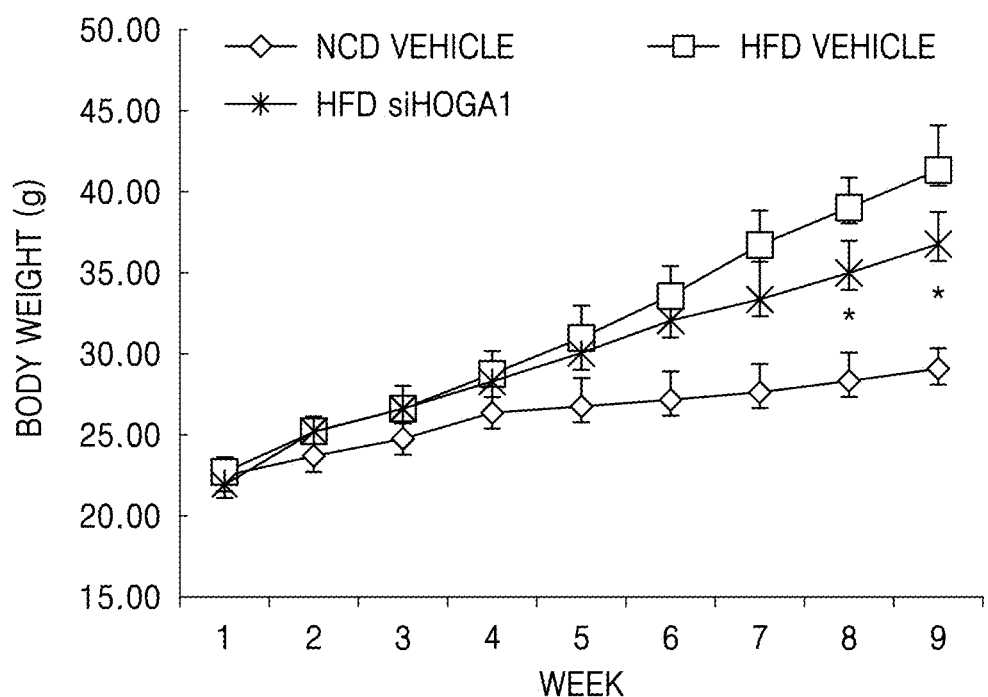
FIG. 4 is a graph showing a change in the body weight of each test group over time.

The food intake and body weight changes of the wild-type and Hoga1 siRNA treated mice according to the normal diet and the high-fat diet for 8 weeks are shown in FIGS. 3 and 4.

FIG. 3 is a graph showing the food intake of mice treated with each of wild-type (NCD vehicle), high-fat diet (HFD vehicle), and a combination of high-fat diet and Hoga1 siRNA (HFD siHOGA1).

FIG. 4 is a graph showing the body weight change of mice treated with each of wild-type (NCD vehicle), high-fat diet (HFD vehicle), and a combination of high-fat diet and Hoga1 siRNA (HFD siHOGA1) over time.

As shown in FIG. 3, there was no significant change in food intake between the high-fat diet group and the Hoga1 siRNA treatment group. As shown in FIG. 4, there was no increase in body weight due to obesity caused by the high-fat diet in Hoga1 siRNA-treated mice.

These results indicate that inhibition of expression of the Hoga1 gene does not affect the subject's health, indicating the safety of the composition according to the present disclosure.

Figure 5:
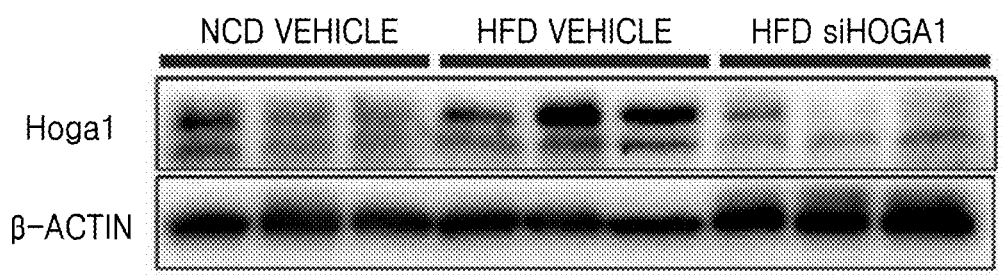
FIG. 5 shows an image of adipose tissues of each test group, of which expression of the Hoga1 protein is confirmed by Western blotting.

Example 4. Analysis of Hoga1 Gene Expression in Adipose Tissue of Obesity-Induced Mice Treated with Hoga1 siRNA The protein of epididymal adipose tissue obtained from the experimental animal of Example 3 was extracted and the expression of Hoga1 was measured by Western blotting. The results are shown in FIG. 5. FIG. 5 shows Western blot analysis of protein expression of Hoga1 in adipose tissue of wild-type mice (NCD vehicle), high-fat diet mice (HFD vehicle), high-fat diet mice treated with Hoga1 siRNA (HFD siHOGA1).

As shown in FIG. 5, the expression of Hoga1 was increased in the epididymal adipose tissue of the high-fat diet group compared to that of the normal diet group. In addition, the expression of Hoga1 in the Hoga1 siRNA-treated group was significantly lower than that in the high-fat diet group.

These results indicate that obesity increases expression of the Hoga1 gene and when the expression thereof is inhibited, the obesity may be treated efficiently.

Example 5. Analysis of Blood Glucose and Insulin Content in Serum of Hoga1 siRNA Treated High-Fat Diet Obesity-Induced Mice Serum obtained from the experimental animals of Example 3 was isolated and the contents of blood glucose and insulin as indicators of type 2 diabetes were measured. The results are shown in FIGS. 6A and 6B.

Figure 6A:
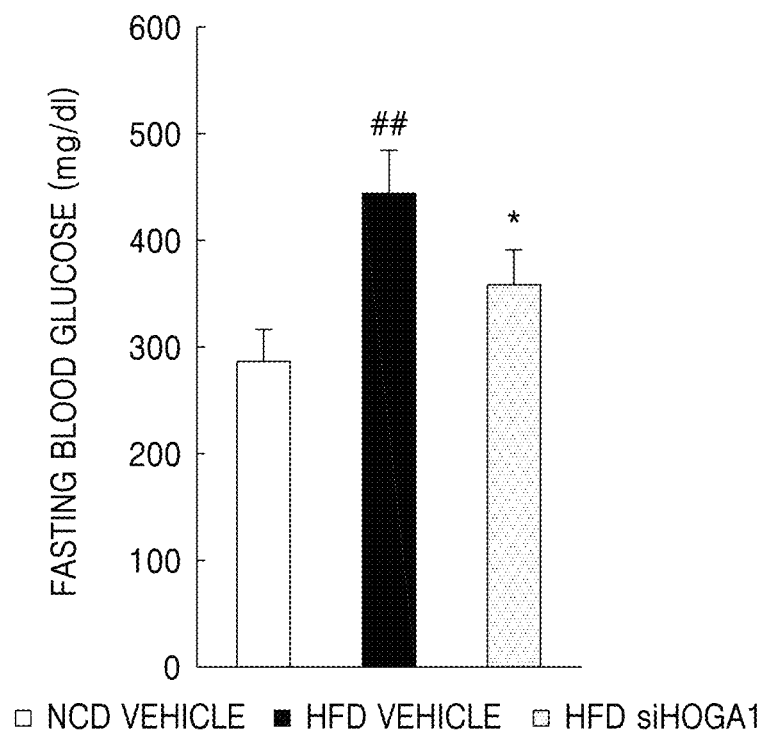
FIG. 6A is a graph showing the content of blood glucose in blood of each test group.
Figure 6B:
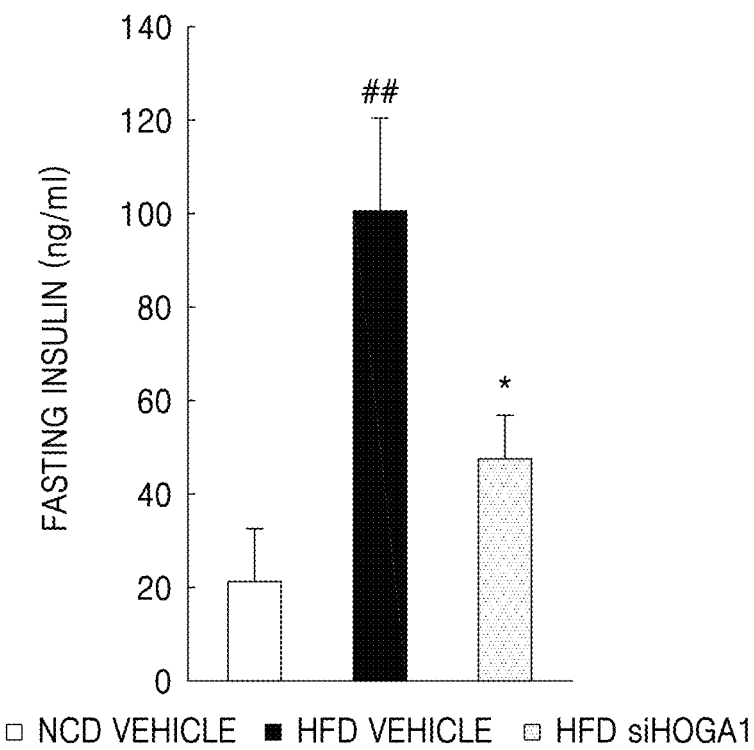
FIG. 6B is a graph showing the content of insulin in blood of each test group.

FIGS. 6A and 6B are graphs showing the contents of blood glucose and insulin of wild-type mice (NCD vehicle), high-fat diet mice (HFD vehicle), high-fat diet mice treated with Hoga1 siRNA (HFD siHOGA1).

As illustrated in FIGS. 6A and 6B, the contents of blood glucose and insulin were increased in the blood (serum) of the high-fat diet-administered group compared to in that of the normal diet group. In addition, the contents of blood glucose and insulin were significantly decreased in the Hoga1 siRNA-treated group compared to in the high-fat diet group. These results indicate that inhibition of expression of the Hoga1 gene is effective in the treatment of diabetes induced by high-fat diets.

Example 6. Analysis of Contents of Serum Triglyceride and Serum Leptin in High-Fat Diet Obesity-Induced Mice Treated with Hoga1 siRNA Serum was isolated from the experimental animals of Example 3 and the contents of serum triglyceride and serum leptin were measured. The results are shown in FIGS. 7A and 7B.

Figure 7A:
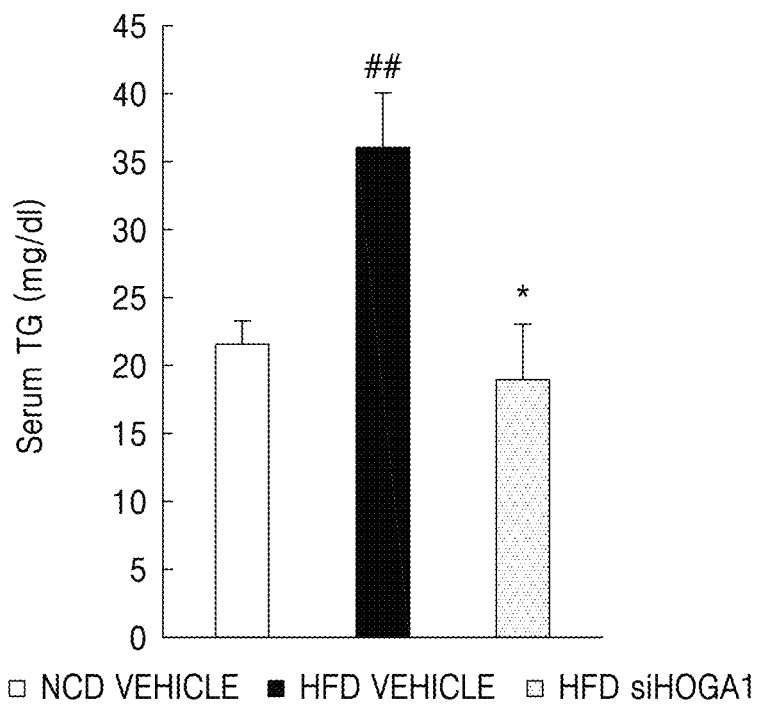
FIG. 7A is a graph showing the content of triglycerides in blood (serum) of each test group.
Figure 7B:
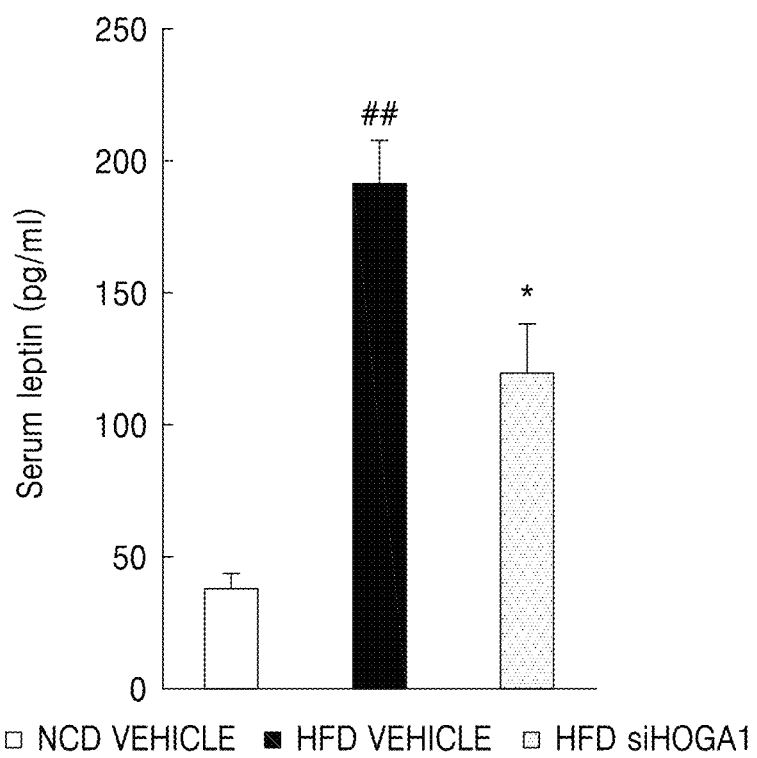
FIG. 7B is a graph showing the content of leptin in blood (serum) of each test group.

FIGS. 7A and 7B are graphs showing the contents of serum triglyceride and serum leptin of wild-type mice (NCD vehicle), high-fat diet mice (HFD vehicle), high-fat diet mice treated with Hoga1 siRNA (HFD siHOGA1).

As illustrated in FIGS. 7A and 7B, the contents of triglyceride and leptin were increased in the serum of the high-fat diet-administered group compared to in the normal diet group. In addition, the contents of triglyceride and leptin were decreased in the Hoga1 siRNA-treated group compared to in the high-fat diet group. These results indicate that inhibition of expression of the Hoga1 gene is highly effective in inhibiting lipid accumulation induced by high-fat diets.

Example 7. Analysis of Inflammatory Cytokines and Chemokines in Serum of High-Fat Diet Obesity-Induced Mice Treated with Hoga1 siRNA Serum was isolated from the experimental animals of Example 3 and the contents of inflammatory cytokines and chemokines in serum were measured. The results are shown in FIG. 8.

Figure 8:
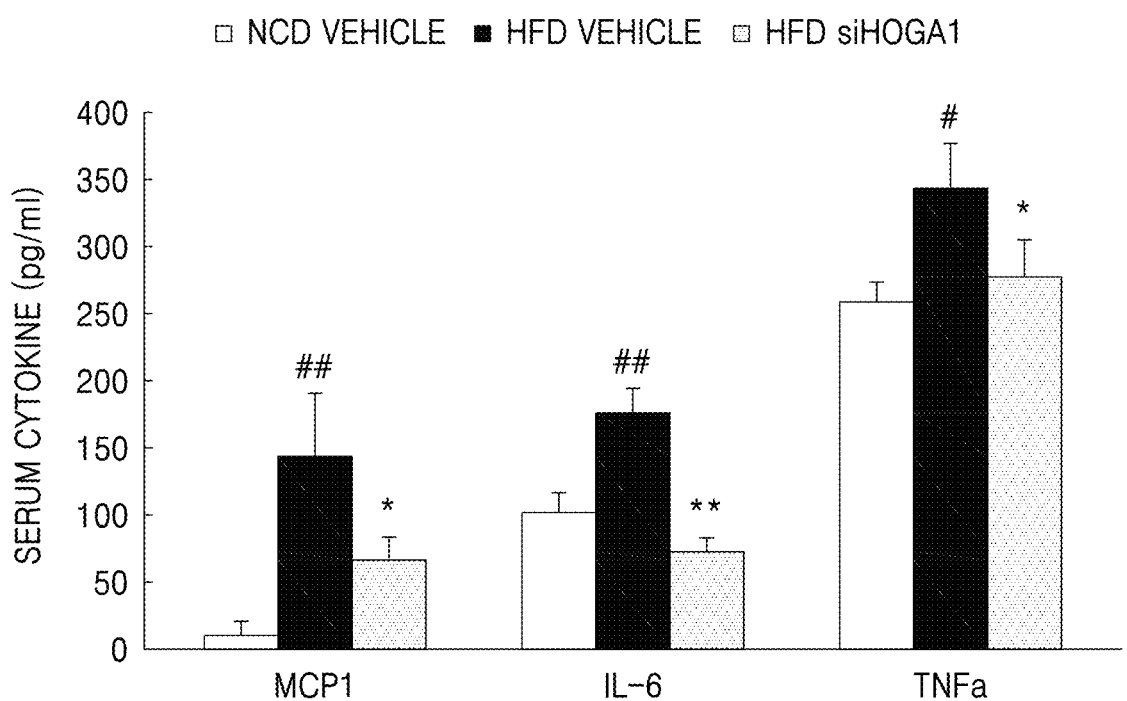
FIG. 8 is a graph obtained by quantifying the content of inflammatory cytokines and chemokines (MCP-1, IL-6, and TNF-α) in the blood of each test group by using ELISA.

FIG. 8 is a graph showing the contents of inflammatory cytokines and chemokines (MCP-1, IL-6, TNF-α) in the blood (serum) of wild-type mice (NCD vehicle), high-fat diet mice (HFD vehicle), high-fat diet mice treated with Hoga1 siRNA (HFD siHOGA1), wherein the contents were quantified by using ELISA.

As shown in FIG. 8, the contents of inflammatory factors, such as MCP-1, IL-6 and TNF-α, were increased in the serum of the high-fat diet-administered group compared to the normal diet group. In addition, the contents of MCP-1, IL-6, and TNF-α in the Hoga1 siRNA-treated group were decreased compared to those of the high-fat diet group. These results indicate that inhibition of expression of the Hoga1 gene is highly effective in inhibiting generation of inflammatory mediators induced by high-fat diets.

Example 8. Analysis of Lipid Accumulation in Liver Tissue of High-Fat Diet Obesity-Induced Mouse Treated with Hoga1 siRNA The liver tissues were isolated from the experimental animals of Example 3 and weighed, and subjected to histological analysis through haematoxylin and eosin (H&E) staining. Liver tissues were first fixed in 10% neutral buffered formalin. The tissue was embedded in paraffin after several successive runs of the graded alcohol series and dehydration through washing. The tissue sections were cut to a thickness of 4 μm and stained with hematoxylin and eosin. The results are shown in FIGS. 9A and 9B.

Figure 9A:
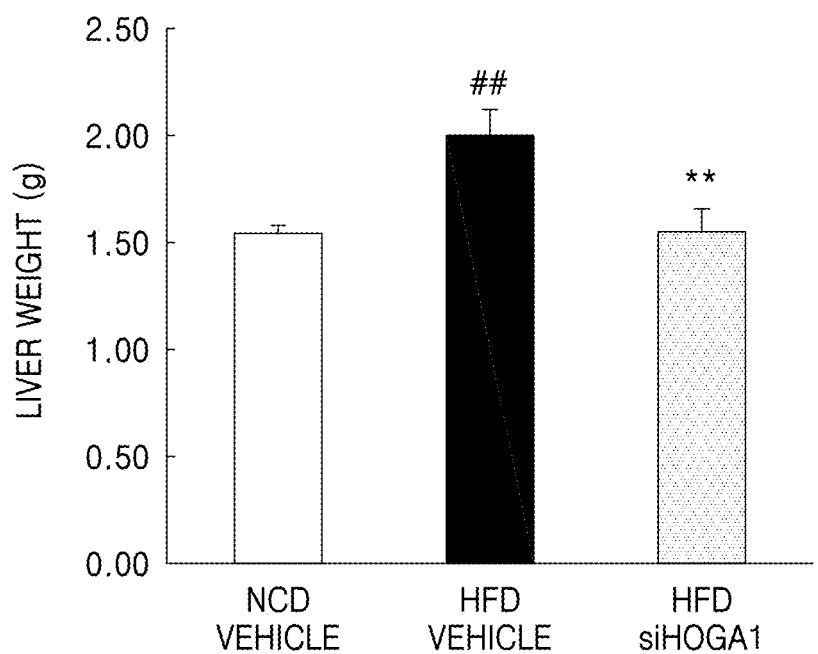
FIG. 9A is a graph showing the liver weight (A) of each test group.
Figure 9B:
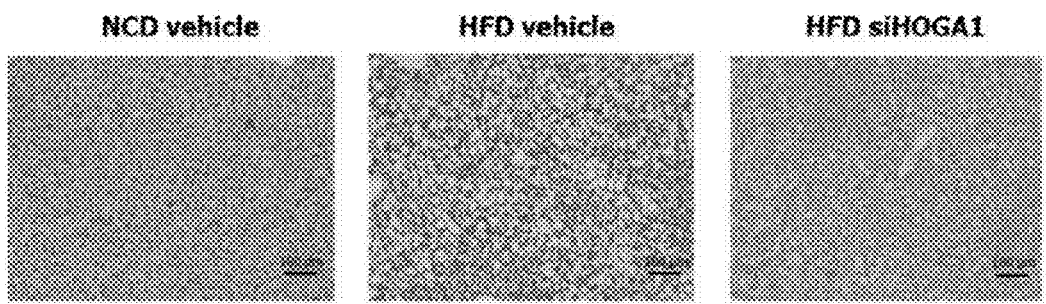
FIG. 9B is a graph showing lipid accumulation (B) in the liver measured by H&E staining of each test group.

FIGS. 9A and 9B are graphs illustrating liver weights (FIG. 9A) of wild-type mice (NCD vehicle), high-fat diet mice (HFD vehicle), and high-fat diet mice treated with Hoga1 siRNA (HFD siHOGA1), and hepatic lipid accumulation (FIG. 9B) of wild-type mice (NCD vehicle), high-fat diet mice (HFD vehicle), and high-fat diet mice treated with Hoga1 siRNA (HFD siHOGA1), which was confirmed by H&E staining.

As shown in FIGS. 9A and 9B, the liver tissue weight and lipid accumulation content of the high-fat diet-administered group were increased compared to those of the normal diet group. In addition, liver tissue weight and lipid accumulation were decreased in the Hoga1 siRNA-treated group compared to in the high-fat diet group. These results indicate that inhibition of expression of the Hoga1 gene is highly effective in inhibiting production of nonalcoholic fatty liver induced by high-fat diets.

Example 9. Analysis of Lipid Accumulation in Adipose Tissue of High-Fat Diet Obesity-Induced Mouse Treated with Hoga1 siRNA The kidney and epididymal adipose tissues were isolated obtained from the experimental animals of Example 3, were weighed, and were subjected to histological analysis through H&E staining and the analysis of expression of factors involved in fatty acid synthesis. Epididymal adipose tissues were fixed in 10% neutral buffered formalin for histological analysis. Graded alcohol series and dehydration through washing were performed several times before the tissues were embedded in paraffin. Tissue sections were cut to a thickness of 4 μm and stained with haematoxylin and eosin. To determine the size of white adipocytes, each section was measured by using opti pro software (Olympus Co., USA) to identify the region of each adipocyte.

RT-PCR assays were performed to analyze the expression of factors related to fatty acid synthesis. In detail, total RNA was harvested from epididymal adipose tissue by using TRIzol reagent (Invitrogen, Carlsbad, Calif., USA) and reverse transcribed, and then RT-PCR was performed thereon as follows. First, for cDNA synthesis, the RNA was reverse transcribed by using reverse transcriptase. RT-PCR was performed by using the specific primers listed in Table 4. The relative mRNA expression level of each gene was normalized to the value of β-actin. The results are shown in FIGS. 10A to 10D.

TABLE 5

| Mice | β-actin | Acaca | Fasn | Lpl | Scd1 | Srebf1 |
|---|---|---|---|---|---|---|
| Forward Primer (F) | SEQ ID NO: 1 | SEQ ID NO: 17 | SEQ ID NO: 19 | SEQ ID NO: 21 | SEQ ID NO: 23 | SEQ ID NO: 25 |
| Reverse Primer (R) | SEQ ID NO: 2 | SEQ ID NO: 18 | SEQ ID NO: 20 | SEQ ID NO: 22 | SEQ ID NO: 24 | SEQ ID NO: 26 |

Figure 10A:
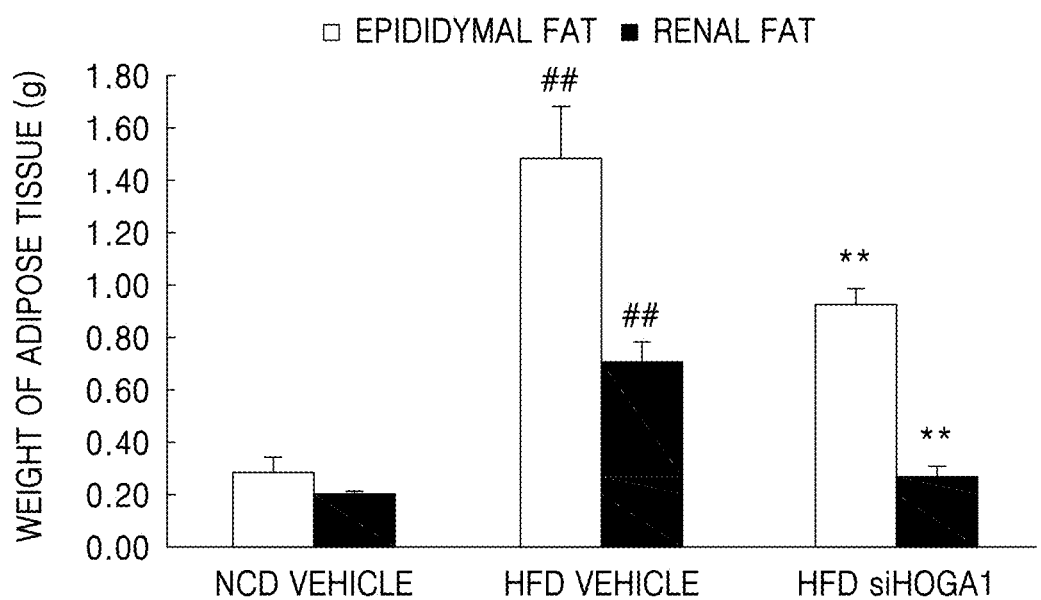
FIG. 10A is a graph showing the weights of the renal fat and epididymal fat of adipose tissues in each test group.
Figure 10B:
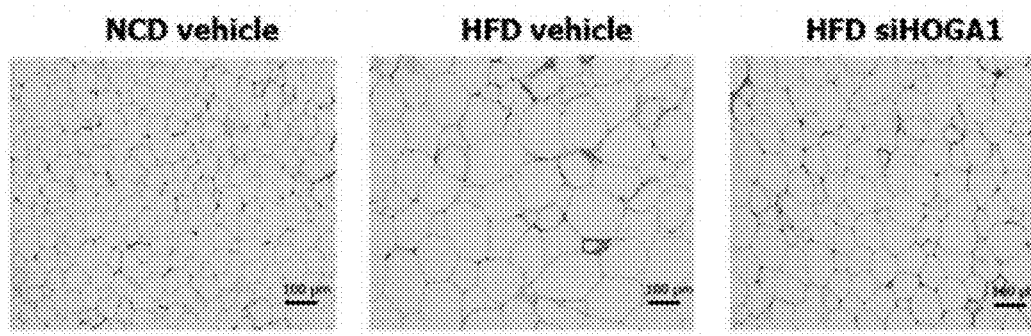
FIGS. 10B and 10C show images and a graph of adipose tissues of each test group in which the sizes of adipocytes measured by H&E staining are shown.
Figure 10C:
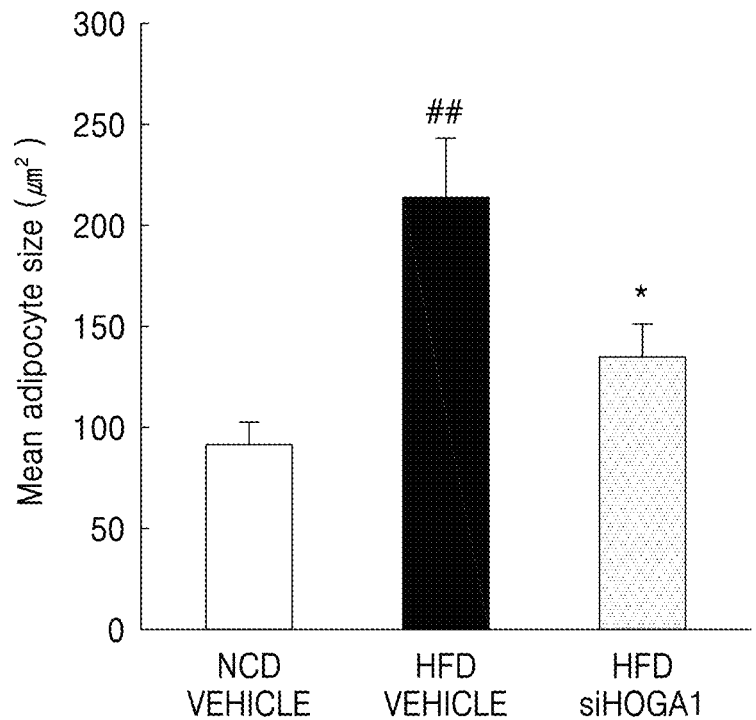
Figure 10D:
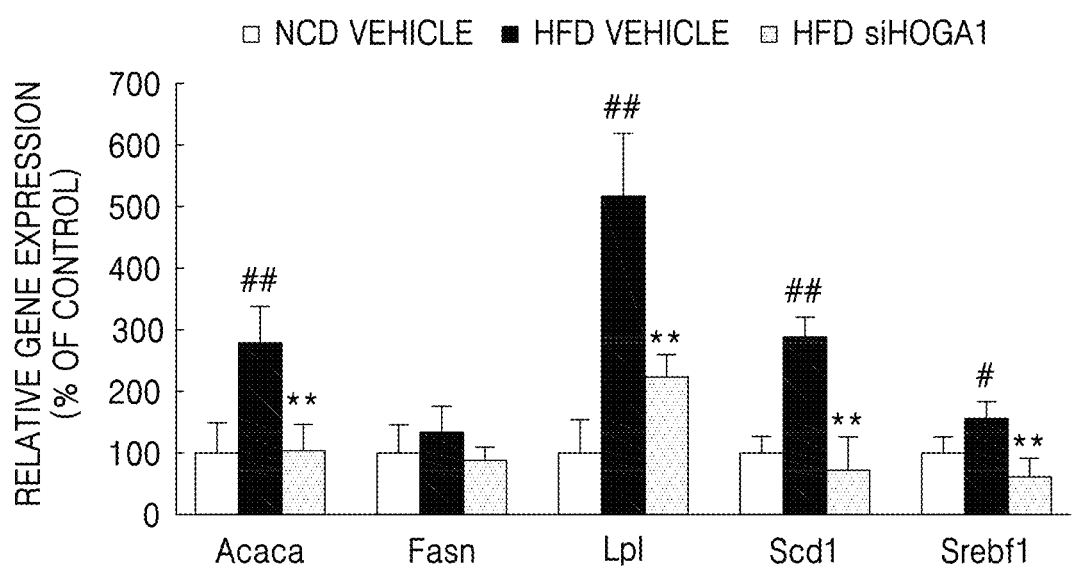
FIG. 10D is a graph obtained by quantifying the expression of fatty acid synthesis factors in adipose tissues by RT-PCR.

FIGS. 10A to 10D are graphs illustrating the anti-obesity effect on adipose tissue of wild-type mice (NCD vehicle), high-fat diet mice (HFD vehicle), high-fat diet mice treated with Hoga1 siRNA (HFD siHOGA1). FIG. 10A is a graph of the weights of the renal fat and epididymal fat of adipose tissues. FIGS. 10B and 10C are graphs showing the adipocyte size obtained by H & E staining of adipose tissue. FIG. 10D is a graph obtained by quantifying the expression of fatty acid synthesis factors, such as Acaca, Fasn, Lpl, Scd1, and Srebf1, in adipose tissue by RT-PCR.

As shown in FIGS. 10A to 10D, the adipose tissue weight, adipocyte size, and fatty acid synthesis factor expression of the high-fat diet-administered group were increased compared with those of the normal diet group. In addition, the adipose tissue weight, adipocyte size, and expression of fatty acid synthesis factors of the Hoga1 siRNA-treated group were smaller than those of the high-fat diet group. These results indicate that inhibition of expression of the Hoga1 gene is highly effective in inhibiting generation of obesity induced by high-fat diets.

According to a composition for the prevention, amelioration, or treatment of obesity including an inhibitor of the expression of Hoga1 gene or an inhibitor of the activity of Hoga1 protein as an active ingredient, a method of screening the composition, and a method of treating obesity by using the composition, obesity can be effectively prevented, ameliorated, or treated.

Hereinbefore, examples of the present disclosure have been described. Those skilled in the art will recognize that the present disclosure may be embodied in various forms without departing from the essential characteristics of the present disclosure. Therefore, the above-described embodiments should be considered in an illustrative aspect rather than a restrictive aspect. The scope of the present disclosure is set forth in the appended claims rather than the foregoing description, and all differences within the scope of equivalents thereof should be construed as being included in the present disclosure.

What is claimed is:

1. A method of preventing or treating obesity, the method comprising administering a composition including an inhibitor of expression of the Hoga1 gene or an inhibitor of activity of the Hoga1 protein.

2. The method of claim 1, wherein the inhibitor of expression of the Hoga1 gene comprises a nucleic acid which specifically binds to the Hoga1 gene.

3. The method of claim 1, wherein the inhibitor of expression of the Hoga1 gene comprises an antisense oligonucleotide, short interfering RNA (siRNA), short hairpin RNA (shRNA), an aptamer, a ribozyme, a low-molecular-weight compound, or a combination thereof, each of which complementarily bind to the mRNA of the Hoga1 gene.

4. The method of claim 1, wherein the inhibitor of expression of the Hoga1 gene comprises an antisense oligonucleotide, an siRNA, an aptamer, or a combination thereof, each of which bind to the Hoga1 gene.

5. The method of claim 1, wherein the inhibitor of activity of the Hoga1 protein comprises a substrate analog, an antibody, or a combination thereof, each of which specifically bind to the Hoga1 protein.

6. The method of claim 1, wherein the inhibitor of activity of the Hoga1 protein comprises an antibody that binds to the Hoga1 protein.

7. The method of claim 1, wherein the composition further comprises a pharmaceutically acceptable carrier.

* * * * *

SEQUENCE LISTING

```
<160> NUMBER OF SEQ ID NOS: 26

<210> SEQ ID NO 1
<211> LENGTH: 20
<212> TYPE: DNA
<213> ORGANISM: Artificial Sequence
<220> FEATURE:
<223> OTHER INFORMATION: Synthetic: forward primer of beta-actin

<400> SEQUENCE: 1
agccatgtac gtagccatcc                                               20

<210> SEQ ID NO 2
<211> LENGTH: 20
<212> TYPE: DNA
<213> ORGANISM: Artificial Sequence
<220> FEATURE:
<223> OTHER INFORMATION: Synthetic: reverse primer of beta-actin

<400> SEQUENCE: 2
ctctcagctg tggtggtgaa                                               20

<210> SEQ ID NO 3
<211> LENGTH: 20
<212> TYPE: DNA
<213> ORGANISM: Artificial Sequence
<220> FEATURE:
<223> OTHER INFORMATION: Synthetic: forward primer of Hoga1

<400> SEQUENCE: 3
tgttgtacag tgtcccagcc                                               20

<210> SEQ ID NO 4
<211> LENGTH: 20
<212> TYPE: DNA
<213> ORGANISM: Artificial Sequence
<220> FEATURE:
<223> OTHER INFORMATION: Synthetic: reverse primer of Hoga1

<400> SEQUENCE: 4
caagacattg gccaagccac                                               20

<210> SEQ ID NO 5
<211> LENGTH: 18
<212> TYPE: RNA
<213> ORGANISM: Artificial Sequence
<220> FEATURE:
<223> OTHER INFORMATION: Synthetic: sense of Control siRNA

<400> SEQUENCE: 5
```
ccuacgccac caauuucg                                                    18

<210> SEQ ID NO 6
<211> LENGTH: 18
<212> TYPE: RNA
<213> ORGANISM: Artificial Sequence
<220> FEATURE:
<223> OTHER INFORMATION: Synthetic: antisense of Control siRNA

<400> SEQUENCE: 6
acgaaauugg uggcguag                                                    18

<210> SEQ ID NO 7
<211> LENGTH: 21
<212> TYPE: RNA
<213> ORGANISM: Artificial Sequence
<220> FEATURE:
<223> OTHER INFORMATION: Synthetic: sense of Mouse Hoga1 siRNA

<400> SEQUENCE: 7
cuucuaaucc uuucaaauau u                                                21

<210> SEQ ID NO 8
<211> LENGTH: 21
<212> TYPE: RNA
<213> ORGANISM: Artificial Sequence
<220> FEATURE:
<223> OTHER INFORMATION: Synthetic: antisense of Mouse Hoga1 siRNA

<400> SEQUENCE: 8
uaagcauuua uauauguuau u                                                21

<210> SEQ ID NO 9
<211> LENGTH: 20
<212> TYPE: DNA
<213> ORGANISM: Artificial Sequence
<220> FEATURE:
<223> OTHER INFORMATION: Synthetic: forward primer of PPARgamma

<400> SEQUENCE: 9
gggctgagga gaagtcacac                                                  20

<210> SEQ ID NO 10
<211> LENGTH: 20
<212> TYPE: DNA
<213> ORGANISM: Artificial Sequence
<220> FEATURE:
<223> OTHER INFORMATION: Synthetic: reverse primer of PPARgamma

<400> SEQUENCE: 10
ggaatgcgag tggtcttcca                                                  20

<210> SEQ ID NO 11
<211> LENGTH: 20
<212> TYPE: DNA
<213> ORGANISM: Artificial Sequence
<220> FEATURE:
<223> OTHER INFORMATION: Synthetic: forward primer of aP2

<400> SEQUENCE: 11
tggaagacag ctcctcctcg                                                  20

<210> SEQ ID NO 12
<211> LENGTH: 21
<212> TYPE: DNA

```
<213> ORGANISM: Artificial Sequence
<220> FEATURE:
<223> OTHER INFORMATION: Synthetic: reverse primer of aP2

<400> SEQUENCE: 12
ccgccatcta gggttatgat g                                           21

<210> SEQ ID NO 13
<211> LENGTH: 20
<212> TYPE: DNA
<213> ORGANISM: Artificial Sequence
<220> FEATURE:
<223> OTHER INFORMATION: Synthetic: forward primer of CD36

<400> SEQUENCE: 13
tgaatggttg agaccccgtg                                             20

<210> SEQ ID NO 14
<211> LENGTH: 20
<212> TYPE: DNA
<213> ORGANISM: Artificial Sequence
<220> FEATURE:
<223> OTHER INFORMATION: Synthetic: reverse primer of CD36

<400> SEQUENCE: 14
tacgtggccc ggttctacta                                             20

<210> SEQ ID NO 15
<211> LENGTH: 19
<212> TYPE: DNA
<213> ORGANISM: Artificial Sequence
<220> FEATURE:
<223> OTHER INFORMATION: Synthetic: forward primer of C/EBPalpha

<400> SEQUENCE: 15
ctgcccctca gtccctgtc                                              19

<210> SEQ ID NO 16
<211> LENGTH: 19
<212> TYPE: DNA
<213> ORGANISM: Artificial Sequence
<220> FEATURE:
<223> OTHER INFORMATION: Synthetic: reverse primer of C/EBPalpha

<400> SEQUENCE: 16
gttccttcag caacagcgg                                              19

<210> SEQ ID NO 17
<211> LENGTH: 20
<212> TYPE: DNA
<213> ORGANISM: Artificial Sequence
<220> FEATURE:
<223> OTHER INFORMATION: Synthetic: forward primer of Acaca

<400> SEQUENCE: 17
cgagtcctct cctcagctcc                                             20

<210> SEQ ID NO 18
<211> LENGTH: 20
<212> TYPE: DNA
<213> ORGANISM: Artificial Sequence
<220> FEATURE:
<223> OTHER INFORMATION: Synthetic: reverse primer of Acaca

<400> SEQUENCE: 18
atcgggagtg ctggtttagc                                             20
```

<210> SEQ ID NO 19
<211> LENGTH: 20
<212> TYPE: DNA
<213> ORGANISM: Artificial Sequence
<220> FEATURE:
<223> OTHER INFORMATION: Synthetic: forward primer of Fasn

<400> SEQUENCE: 19
caagtgtcca ccaacaagcg                                                20

<210> SEQ ID NO 20
<211> LENGTH: 20
<212> TYPE: DNA
<213> ORGANISM: Artificial Sequence
<220> FEATURE:
<223> OTHER INFORMATION: Synthetic: reverse primer of Fasn

<400> SEQUENCE: 20
ggagcgcagg atagactcac                                                20

<210> SEQ ID NO 21
<211> LENGTH: 20
<212> TYPE: DNA
<213> ORGANISM: Artificial Sequence
<220> FEATURE:
<223> OTHER INFORMATION: Synthetic: forward primer of Lpl

<400> SEQUENCE: 21 aagcccaca agtgtagtcg                                                 20

<210> SEQ ID NO 22
<211> LENGTH: 20
<212> TYPE: DNA
<213> ORGANISM: Artificial Sequence
<220> FEATURE:
<223> OTHER INFORMATION: Synthetic: reverse primer of Lpl

<400> SEQUENCE: 22
ataatgggga tgccggtgac                                                20

<210> SEQ ID NO 23
<211> LENGTH: 21
<212> TYPE: DNA
<213> ORGANISM: Artificial Sequence
<220> FEATURE:
<223> OTHER INFORMATION: Synthetic: forward primer of Scd1

<400> SEQUENCE: 23
tgagctttgg gcttctgagt t                                              21

<210> SEQ ID NO 24
<211> LENGTH: 20
<212> TYPE: DNA
<213> ORGANISM: Artificial Sequence
<220> FEATURE:
<223> OTHER INFORMATION: Synthetic: reverse primer of Scd1

<400> SEQUENCE: 24
caaacaggga ctgagcacca                                                20

<210> SEQ ID NO 25
<211> LENGTH: 20
<212> TYPE: DNA
<213> ORGANISM: Artificial Sequence
<220> FEATURE:

```
<223> OTHER INFORMATION: Synthetic: forward primer of Srebf1

<400> SEQUENCE: 25
cagactcact gctgctgaca                                                    20

<210> SEQ ID NO 26
<211> LENGTH: 19
<212> TYPE: DNA
<213> ORGANISM: Artificial Sequence
<220> FEATURE:
<223> OTHER INFORMATION: Synthetic: reverse primer of Srebf1

<400> SEQUENCE: 26
cctccactca ccagggtct                                                     19
```